(12) United States Patent
Al Seraihi et al.

(10) Patent No.: US 10,703,987 B2
(45) Date of Patent: Jul. 7, 2020

(54) METHODS AND SYSTEMS FOR PROACTIVELY MONITORING CRUDE QUALITY ASSURANCE

(71) Applicant: Saudi Arabian Oil Company, Dhahran (SA)

(72) Inventors: Emad Fahd Al Seraihi, Dhahran (SA); Adeeb Hassan AlBukhari, Dhahran (SA); Saad Younes Mousa, Dhahran (SA); Khaled Khalifah Al-Yousef, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 293 days.

(21) Appl. No.: 15/691,932

(22) Filed: Aug. 31, 2017

(65) Prior Publication Data

US 2019/0062645 A1  Feb. 28, 2019

(51) Int. Cl.
| | |
|---|---|
| *C10G 31/08* | (2006.01) |
| *C10G 33/00* | (2006.01) |
| *B01D 11/04* | (2006.01) |
| *B01D 17/02* | (2006.01) |
| *B01D 17/04* | (2006.01) |
| *B01D 17/12* | (2006.01) |

(Continued)

(52) U.S. Cl.
CPC .......... *C10G 31/08* (2013.01); *B01D 11/0446* (2013.01); *B01D 11/0484* (2013.01); *B01D 17/02* (2013.01); *B01D 17/047* (2013.01); *B01D 17/12* (2013.01); *C10G 33/00* (2013.01); *C10G 33/08* (2013.01); *C10G 2300/205* (2013.01); *G01N 33/2823* (2013.01)

(58) Field of Classification Search
None
See application file for complete search history.

(56) References Cited

U.S. PATENT DOCUMENTS

| | | |
|---|---|---|
| 4,581,134 A | 4/1986 | Richter, Jr. et al. |
| 5,612,490 A | 3/1997 | Carlson et al. |

(Continued)

FOREIGN PATENT DOCUMENTS

WO  2017023858 A1  2/2017

OTHER PUBLICATIONS

Alshehri, A., Modeling and Optimization of Desalting Process in Oil Industry, 2009, Thesis, University of Waterloo. (Year: 2009).*

(Continued)

*Primary Examiner* — Derek N Mueller
(74) *Attorney, Agent, or Firm* — Bracewell LLP; Constance G. Rhebergen; Brian H. Tompkins (57) ABSTRACT

Methods and systems to monitor and control crude oil processing with regards to crude oil specifications for bottom sediment & water (BS&W) and salt are provided. Crude oil processing may be monitored and controlled using key performance indicators (KPIs) that include the desalter voltage and dehydrator voltage as indicators of the BS&W and salt. In response to monitoring of the desalter voltage and dehydrator voltage, a high pressure production trap (HPPT) efficiency and a dehydrator separation efficiency may be controlled via adjustment of a wash water percentage, a demulsifier dosage, a dehydrator interface level, a desalter interface level, and a differential pressure across a mixing valve.

26 Claims, 5 Drawing Sheets

(51) Int. Cl.
*C10G 33/08* (2006.01)
*G01N 33/28* (2006.01)

(56) References Cited

U.S. PATENT DOCUMENTS

| | | |
|---|---|---|
| 8,747,658 B2 | 6/2014 | Love |
| 9,092,124 B2 | 6/2015 | Amminudin et al. |
| 9,181,499 B2 | 11/2015 | Mason et al. |
| 9,255,228 B2 | 2/2016 | Prasad et al. |
| 9,347,009 B2 | 5/2016 | Kusinski et al. |
| 9,457,296 B2 | 10/2016 | Jansen et al. |
| 9,493,712 B2 | 11/2016 | Barroeta et al. |
| 2011/0089082 A1 | 4/2011 | Snawerdt |
| 2011/0100877 A1 | 5/2011 | Snawerdt |
| 2014/0131254 A1 | 5/2014 | Soliman |
| 2014/0202923 A1 | 7/2014 | Kremer et al. |
| 2016/0060546 A1 | 3/2016 | Collins, Jr. et al. |

OTHER PUBLICATIONS

International Search Report and Written Opinion for related PCT application PCT/US2018/049016 dated Nov. 14, 2018; pp. 1-15.

\* cited by examiner

| PERFORMANCE MEASURE | TAG SOURCE | RANGE 1 MIN | RANGE 1 MAX | RANGE 2 MIN | RANGE 2 MAX | RANGE 3 MIN | RANGE 3 MAX | TAG VALUE | RADIAL GAUGE DISPLAY |
|---|---|---|---|---|---|---|---|---|---|
| HTTP SEPARATION EFFICIENCY | ABQC_OQ_ANDR1-HPPTs-efficiency.cal | 0:00 | 45:00 | 45:00-00 | 60:00-00 | 60:00-00 | 150:00-00 | 1.58 | |
| HTTP SEPARATION EFFICIENCY | ABQC_OQ_ANDR1-HPPTs-efficiency.cal | 0:00 | 15:00 | 15:00-00 | 25:00-00 | 25:00-00 | 50:00-00 | 12.47 | |
| CRUDE OIL HEADER TEMPERATURE | ABQC_OQ_ANDR1-TL-3010.PV | 0:00 | 100:00 | 100:00-00 | 120:00-00 | 120:00-00 | 160:00-00 | 159.04 | |
| DEMULSIFIER DOSAGE RATE PPM | ABQC_OQ_ANDR1-Demulsifier-rate.cal | 0:00 | 15:00 | 15:00-00 | 20:00-00 | 20:00-00 | 30:00-00 | 4.82 | |
| DEMULSIFIER DOSAGE RATE GDP | ABQC_OQ_ANDR1-FIC-533A.PV | 0:00 | 30:00 | 30:00-00 | 40:00-00 | 40:00-00 | 100:00-00 | 46.7 | |
| DEMULSIFIER DOSAGE RATE GDP | ABQC_OQ_ANDR1-Dehydrator-effecincy.cal | 0:00 | 40:00 | 40:00-00 | 55:00-00 | 55:00-00 | 100:00-00 | 44.77 | |
| CRUDE OIL BS&W TO PIPELINE | ABQC_OQ_ANDR1-:AI-3010.PV | 0:00 | 0:15 | 0:15-00 | 0:20-00 | 0:20-00 | 0:25-00 | 0.04 | |

FIG. 5

METHODS AND SYSTEMS FOR PROACTIVELY MONITORING CRUDE QUALITY ASSURANCE

BACKGROUND

Field of the Disclosure

The present disclosure generally relates to the processing of crude oil. More specifically, embodiments of the disclosure relate to processing monitoring and control for crude oil quality assurance.

Description of the Related Art

The production of crude oil may involve a number of processes engineered to produce crude oil to specific quality specifications. For example, such quality specifications may specify a maximum amount of salt and basic sediment and water (BS&W) permitted in crude oil. The production of crude oil may thus include processing to remove salt and BS&W. In some instances, for example, the amount of salt and BS&W in produced crude oil may be directly monitored by sampling crude oil from a pipeline at time intervals. However, such sampling may only be reactively change process parameters to improve crude oil quality. Moreover, such direct sampling may be tedious and time-consuming, and such sampling may only detect deterioration in crude oil quality after it has occurred in the time interval between samplings. Further, the existing process parameters used to adjust the BS&W and salt in processed crude oil may not efficiently control the desalting process.

SUMMARY

Embodiments of the disclosure generally relate to the monitor and control of crude oil processing with regards to crude oil specifications for bottom sediment & water (BS&W) and salt in the processed crude oil.

In one embodiment, a method of processing crude oil is provided that includes obtaining a voltage associated with a desalter of a crude oil processing system and obtaining a voltage associated with a dehydrator of a crude oil processing system, such that an output stream from the dehydrator is provided to the desalter. The method further includes evaluating at least one of the first voltage and the second voltage as an indicator of the salt concentration in crude oil and adjusting at least one of a plurality of control parameters in response to the evaluation to modify at least one of a separation efficiency of a high pressure production trap (HPPT) of the crude oil processing system and a separation efficiency of the dehydrator. The plurality of control parameters include a wash water parameter, a demulsifier parameter, an interface level of the dehydrator, an interface level of the desalter, and a mixing valve parameter.

In some embodiments, evaluating at least one of the first voltage and the second voltage includes comparing at least one of the first voltage and the second voltage to a voltage threshold. In some embodiments, evaluating at least one of the first voltage and the second voltage includes comparing at least one of the first voltage and the second voltage to a first operating voltage range, a second operating voltage range, and a third operating voltage range. In some embodiments, the wash water parameter includes a ratio of the a wash water flow rate to the a dry crude oil flowrate, such that the dry crude oil flowrate is a flowrate of crude oil downstream from the desalter. In some embodiments, the dehydrator output stream is mixed with a demulsifier before being provided to the desalter. In such embodiments, the demulsifier parameter includes a ratio of a demulsifier flowrate to a sum of a dry crude oil flowrate and a produced water flowrate minus a wash water flowrate, such that the dry crude oil flowrate is a flowrate of crude oil downstream from the desalter and the produced water flowrate is a flowrate of separated water from the dehydrator and the HPPT after the separated water is provided to a water-oil separation unit. In some embodiments, the mixing valve parameter is a differential pressure across a mixing value positioned to mix wash water, a demulsifier, and the dehydrator output stream. In some embodiments, the separation efficiency of the high pressure production trap (HPPT) is the ratio of HPPT water outlet flowrate to a difference between a produced water flowrate and a wash water flowrate, such that the produced water flowrate is a flowrate of separated water from the dehydrator and the HPPT after the separated water is provided to a water-oil separation unit. In some embodiments, the separation efficiency of the dehydrator is the ratio of dehydrator water outlet flowrate to a difference between a produced water flowrate and a wash water flowrate, such that the produced water flowrate is a flowrate of separated water from the dehydrator and the HPPT after the separated water is provided to a water-oil separation unit. In some embodiments, adjusting at least one of the plurality of control parameters includes adjusting at least one of the plurality of control parameters in response to the temperature of a crude oil feed to the crude oil processing facility. In some embodiments, adjusting the at least one of a plurality of control parameters includes adjusting at least one of the plurality of control parameters until the adjusted control parameter is within an operating range associated with the adjusted control parameter.

In another embodiment, a non-transitory computer-readable storage medium having executable code stored thereon for controlling the processing crude oil is provided. The executable code includes a set of instructions that causes a processor to perform operations that include obtaining a voltage associated with a desalter of a crude oil processing system and obtaining a voltage associated with a dehydrator of a crude oil processing system, such that an output stream from the dehydrator is provided to the desalter. The operations further include evaluating at least one of the first voltage and the second voltage as an indicator of the salt concentration in crude oil and adjusting at least one of a plurality of control parameters in response to the evaluation to modify at least one of a separation efficiency of the high pressure production trap (HPPT) of the crude oil processing system and a separation efficiency of the dehydrator. The plurality of control parameters include a wash water parameter, a demulsifier parameter, an interface level of the dehydrator, an interface level of the desalter, and a mixing valve parameter.

In some embodiments, evaluating at least one of the first voltage and the second voltage includes comparing at least one of the first voltage and the second voltage to a voltage threshold. In some embodiments, evaluating at least one of the first voltage and the second voltage includes comparing at least one of the first voltage and the second voltage to a first operating voltage range, a second operating voltage range, and a third operating voltage range. In some embodiments, the wash water parameter includes a ratio of the a wash water flow rate to the a dry crude oil flowrate, such that the dry crude oil flowrate is a flowrate of crude oil downstream from the desalter. In some embodiments, the dehydrator output stream is mixed with a demulsifier before being provided to the desalter. In such embodiments, the demulsifier parameter includes a ratio of a demulsifier flowrate to a sum of a dry crude oil flowrate and a produced water flowrate minus a wash water flowrate, such that the dry crude oil flowrate is a flowrate of crude oil downstream from the desalter and the produced water flowrate is a flowrate of separated water from the dehydrator and the HPPT after the separated water is provided to a water-oil separation unit. In some embodiments, the mixing valve parameter is a differential pressure across a mixing value positioned to mix wash water, a demulsifier, and the dehydrator output stream. In some embodiments, the separation efficiency of the high pressure production trap (HPPT) is the ratio of HPPT water outlet flowrate to a difference between a produced water flowrate and a wash water flowrate, such that the produced water flowrate is a flowrate of separated water from the dehydrator and the HPPT after the separated water is provided to a water-oil separation unit. In some embodiments, the separation efficiency of the dehydrator is the ratio of dehydrator water outlet flowrate to a difference between a produced water flowrate and a wash water flowrate, such that the produced water flowrate is a flowrate of separated water from the dehydrator and the HPPT after the separated water is provided to a water-oil separation unit. In some embodiments, adjusting at least one of the plurality of control parameters includes adjusting at least one of the plurality of control parameters in response to the temperature of a crude oil feed to the crude oil processing facility. In some embodiments, adjusting the at least one of a plurality of control parameters includes adjusting at least one of the plurality of control parameters until the adjusted control parameter is within an operating range associated with the adjusted control parameter. In some embodiments, the operations further include providing a graphical user interface on a display coupled to the processor, the graphical user interface having a user interface element graphically indicating the value of the parameter relative to a plurality of operational ranges. In some embodiments, the user interface element includes a first color associated with a first range of the plurality of operating ranges, a second color associated with a second range of the plurality of operating ranges, and a third color associated with a third range of the plurality of operating ranges.

In another embodiment, a crude oil processing system is provided. The crude oil processing system includes a desalter, a dehydrator, a high pressure production trap (HPPT), a processor, and a non-transitory computer-readable memory coupled to the processor and having executable code stored thereon for controlling the processing of crude oil. The executable code includes a set of instructions that causes a processor to perform operations that include obtaining a voltage associated with the desalter and obtaining a voltage associated with the dehydrator. The operations further include evaluating at least one of the first voltage and the second voltage as an indicator of the salt concentration in the crude oil and adjusting at least one of a plurality of control parameters in response to the evaluation to modify at least one of a separation efficiency of the HPPT and a separation efficiency of the dehydrator. The plurality of control parameters include a wash water parameter, a demulsifier parameter, an interface level of the dehydrator, an interface level of the desalter, and a mixing valve parameter. In some embodiments, evaluating at least one of the first voltage and the second voltage includes comparing at least one of the first voltage and the second voltage to a voltage threshold. In some embodiments, evaluating at least one of the first voltage and the second voltage includes comparing at least one of the first voltage and the second voltage to a first operating voltage range, a second operating voltage range, and a third operating voltage range. In some embodiments, the wash water parameter includes a ratio of the a wash water flow rate to the a dry crude oil flowrate, such that the dry crude oil flowrate is a flowrate of crude oil downstream from the desalter. In some embodiments, the dehydrator output stream is mixed with a demulsifier before being provided to the desalter. In such embodiments, the demulsifier parameter includes a ratio of a demulsifier flowrate to a sum of a dry crude oil flowrate and a produced water flowrate minus a wash water flowrate, such that the dry crude oil flowrate is a flowrate of crude oil downstream from the desalter and the produced water flowrate is a flowrate of separated water from the dehydrator and the HPPT after the separated water is provided to a water-oil separation unit. In some embodiments, the mixing valve parameter is a differential pressure across a mixing value positioned to mix wash water, a demulsifier, and the dehydrator output stream. In some embodiments, the separation efficiency of the high pressure production trap (HPPT) is the ratio of HPPT water outlet flowrate to a difference between a produced water flowrate and a wash water flowrate, such that the produced water flowrate is a flowrate of separated water from the dehydrator and the HPPT after the separated water is provided to a water-oil separation unit. In some embodiments, the separation efficiency of the dehydrator is the ratio of dehydrator water outlet flowrate to a difference between a produced water flowrate and a wash water flowrate, such that the produced water flowrate is a flowrate of separated water from the dehydrator and the HPPT after the separated water is provided to a water-oil separation unit.

BRIEF DESCRIPTION OF THE DRAWINGS

FIG. 5 is a screen of an example dashboard graphical user interface (GUI) in accordance with an embodiment of the disclosure;

DETAILED DESCRIPTION

The present disclosure will be described more fully with reference to the accompanying drawings, which illustrate embodiments of the disclosure. This disclosure may, however, be embodied in many different forms and should not be construed as limited to the illustrated embodiments. Rather, these embodiments are provided so that this disclosure will be thorough and complete, and will fully convey the scope of the disclosure to those skilled in the art.

Embodiments of the disclosure include methods and systems to monitor and control crude oil processing with regards to crude oil specifications for bottom sediment & water (BS&W) and salt in the crude oil. As discussed in the disclosure, the performance of a desalter transformer and a dehydrator transformer are monitored via a respective desalter voltage and dehydrator voltage. As discussed below, crude oil processing may be monitored and controlled using key performance indicators (KPIs) that include the desalter voltage and dehydrator voltage. As used herein, the term "key performance indicator" or KPI refers to a parameter associated with a crude oil processing system.

The KPIs may be categorized into monitor KPIs that are directly monitored, target KPIs that are used targets in response to the monitor KPIs, control KPIs that are controlled in response to the monitoring, a feedback KPI used for further adjustment of the control KPIs, and result KPIs that may be used to validate the BS&W and salt content but are not used to control the process. The monitor KPIs may include a desalter voltage and a dehydrator voltage. The target KPIs may include a high pressure production trap (HPPT) efficiency and a dehydrator separation efficiency. The control KPIs may include a wash water percentage, a demulsifier dosage, a dehydrator interface level, a desalter interface level, and a differential pressure across a mixing valve. The feedback KPI may include a temperature of the crude oil feed to a crude oil processing system. The result KPIs may include BS&W content and salt content as directly measured, such as via instruments or lab analysis from a sample of processed crude oil.

In some embodiments, each of the KPIs may be evaluated by comparison to one or more specific operating ranges. In some embodiments, a KPI may be evaluated by comparing the KPI to three operating ranges, designated as of "leading proactive," "lagging proactive", and "lagging reactive." For example, based on the comparison of the monitor KPIs and target KPIs to their respective operating ranges, the control KPIs may be adjusted to ensure that that target KPIs fall within a specific operating range. It should be appreciated that in other embodiments, other KPI evaluations may be performed. For example, in some embodiments, a KPI may be compared to a threshold value to determine whether the KPI is above or below the threshold value.

Advantageously, the use of the monitor KPIs of the dehydrator voltage and the desalter voltage provides a more accurate and predictive indicator of the BS&W and salt content in the processed crude oil, as opposed to direct measurement of the BS&W and salt content in the processed crude oil via instruments or laboratory analysis. The use of the monitor KPIs of the dehydrator voltage and the desalter voltage as an indicator of BS&W and salt content may also provide more time for corrective action (for example, adjustment of one or more of the control KPIs) as compared to direct measurement of the BS&W and salt content in the processed crude oil. In some embodiments, the use of use of the monitor KPIs of the dehydrator voltage and the desalter voltage and corresponding adjustment of the control KPIs may reduce water usage of a crude oil processing system by at least 50%.

Figure 1:
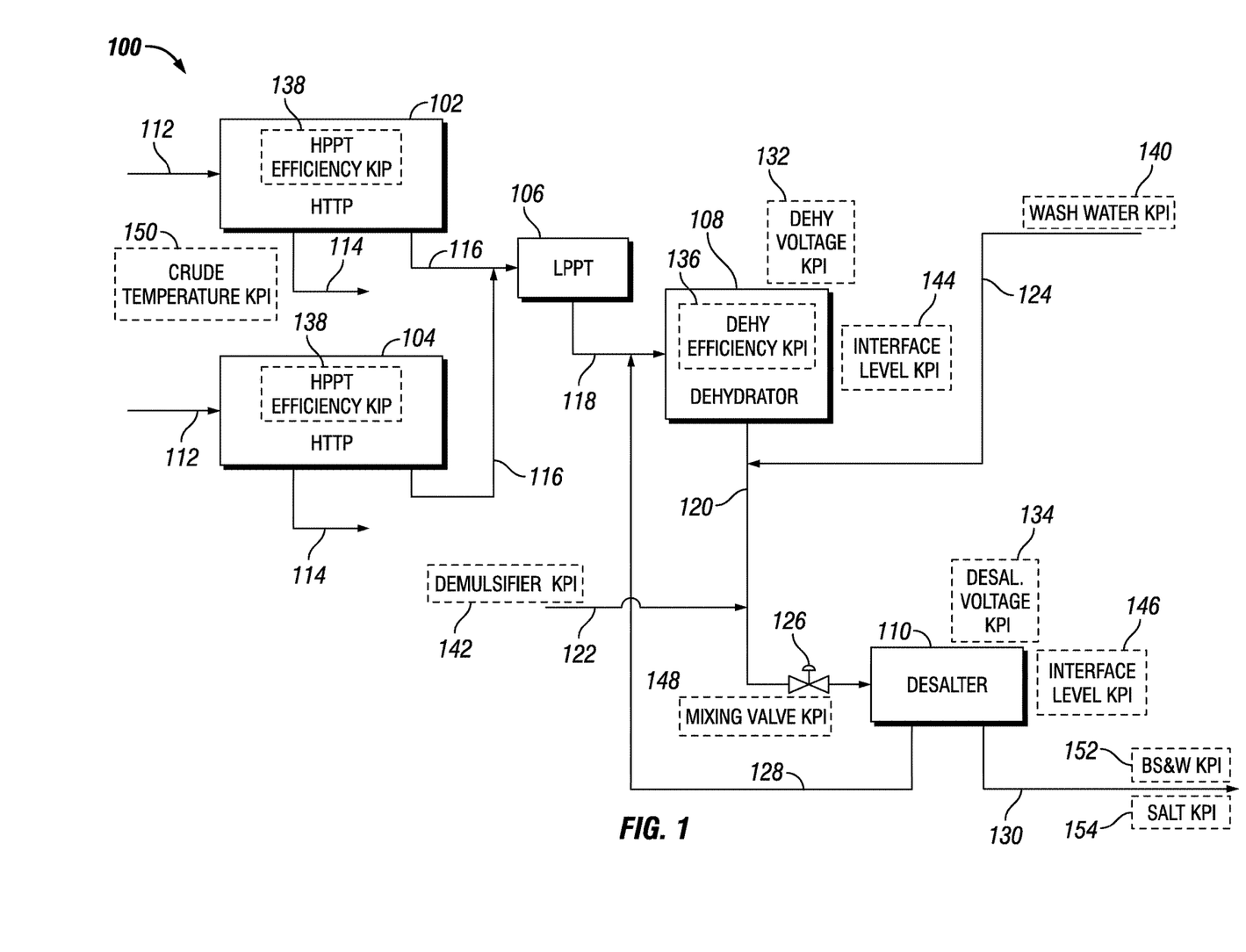
FIG. 1 is a block diagram of a crude oil processing system in accordance with an embodiment of the disclosure.

FIG. 1 depicts an example crude oil processing system 100 in accordance with an embodiment of the disclosure. The depicted crude oil processing system 100 may be representative of, for example, a crude oil processing plant that receives a crude oil feed and produced processed crude oil having reduced amounts of BS&W and salt as compared to the feed. It should be appreciated that the crude oil processing system 100 depicted in FIG. 1 is an example and is simplified for clearer illustration of the embodiments of the disclosure. As will be appreciated, some embodiments may include crude oil processing systems that include additional components to those shown in FIG. 1 or omit one or more of the components shown in FIG. 1.

The example crude oil processing system 100 shown in FIG. 1 includes a first high pressure production trap (HPPT) 102, a second HPPT 104 a low pressure production trap (LPPT) 106, a dehydrator 108, and a desalter 110. Crude oil feeds 112 are provided to the HPPTs 102 and 104 to separate oil, gas, and water in the crude oil feeds 112 at a high pressure as is known in the art. Separated water 114 and separated oil 116 exits the HPPTs 102 and 104. The separated gas (not shown) from the HPPTs 102 and 104 may be provided to a compression train or other units for gas processing.

The crude oil 116 output from the HPPTs 102 and 104 is provided to the LPPT 106 for further separation of oil, gas, and water at a low pressure as is known in the art. The crude oil 118 output from the LPPT 106 is provided to the dehydrator 108 for removal of formation water from the crude oil as is known in the art. Separated gas (not shown) exits the LPPT 106 and may be combined with the separated gas from the HPPTs 102 and 104 and routed to gas processing units.

The crude oil 120 output from the dehydrator 108 is provided to the desalter 110. Separated water (not shown) may also exit the dehydrator 108. In some embodiments, the separated water exiting the HPPTs 102 and 104 and the dehydrator 108 may be routed to a water-oil separation unit as known in the art then to water pumps for injection back in a reservoir or disposal wells. In such embodiments, the separated water exiting the HPPTs 102 and 104 and the dehydrator 108 may be referred to as "produced water."

A demulsifier 122 and wash water 124 are provided for use by the desalter 110 and mixed with the crude oil 120 via a mixing valve 126. The desalter 110 removes salt from the crude oil using suitable techniques known in the art to produce processed crude oil 130 having reduced BS&W and salt content as compared to the crude oil feed 112. Separated water 128 exits the desalter 110 and, as shown in FIG. 1, may be recirculated and mixed with the crude oil 118 provided to the dehydrator 108. The processed crude oil 130 output from the desalter 110 may be routed for further processing (for example, to a crude stabilization unit). In some embodiments, the processed crude oil 130 output from the desalter 110 may be sampled to measure the BS&W and salt content in the crude oil 130. In such embodiments, for example, a portion of the processed crude oil 130 may be obtained and transported to a laboratory or other facility for analysis. As discussed herein, however, embodiments of the disclosure do not use direct measurement of the BS&W and salt content in the processed crude oil 130 to monitor and control the crude oil processing system 100.

FIG. 1 also depicts the KPIs that may be used by embodiments of the disclosure to monitor and control the BS&W and salt content in the processed crude oil 130. As shown FIG. 1, the KPIs may include the dehydrator (dehy.) voltage KPI 132 and the desalter (desal.) voltage KPI 134. The dehydrator voltage KPI 132 may be measured at a transformer of the dehydrator 108, and the desalter voltage KPI 134 may be measured at a transformer of the desalter 110. For example, voltage sensors may be coupled to the transformers of the dehydrator 108 and the desalter 110 and provide the dehydrator transformer voltage (that is, measured in volts) and the desalter transformer voltage (that is, measured in volts) for use as the respective KPIs 132 and 134.

The target KPIs may include the dehydrator efficiency KPI 136 and the HPPT efficiency KPI 138, the determination of which is discussed further below. For example, the dehydrator efficiency KPI 136 and the HPPT efficiency KPI 138 may each be a percentage efficiency. The control KPIs may include the wash water KPI 140, the demulsifier KPI 142, the interface level of the dehydrator 108 (dehydrator interface level KPI 144) the interface level of the desalter 110 (desalter interface level KPI 146), and the differential pressure across the mixing valve 126 (mixing valve KPI 148). The determination of the wash water KPI 140 and demulsifier KPI 142 are discussed further below. For example, the wash water KPI 140 may be percentage, and the demulsifier KPI 142 may be the amount of demulsifier in parts-per-million (ppm) as determined according to the techniques discussed herein. In some embodiments, the demulsifier KPI 142 may also additionally or alternatively be obtained at the crude oil feeds 112 (that is, the demulsifier may be additionally or alternatively be provided at the crude oil feeds 112).

The dehydrator interface level KPI 144 and desalter interface level KPI 146 may be measured directly from the dehydrator and desalter using known components and techniques. For example, as will be appreciated, the dehydrator interface level KPI 144 and desalter interface level KPI 146 may each be percentage value. The mixing valve KPI 148 may be determined via measurement of the pressure across the mixing valve 126 using pressure sensors at the appropriate locations in the crude oil processing system 100. For example, the mixing value KPI 148 may be a pounds-per-square inch gauge (psig) pressure.

The feedback KPI includes the temperature of the crude oil feed stream 112 (crude temperature KPI 150). For example, the crude temperature KPI 150 may be determined by measuring the temperature (for example, in ° F.) of the crude oil feed 112 using one or more temperature sensors positioned at the appropriate locations in the crude oil processing system 100. In some embodiments, the monitor and control of the BS&W and salt content in the processed crude oil 130 may be validated using the directly measured BS&W content (BS&W KPI 152) and salt content (salt KPI 154) which, as noted above, may be directly measured from the processed crude oil 130. For example, the BS&W KPI 152 may be the % volume of BS&W in the processed crude oil 130, and the salt KPI 154 may be the salt content in pounds of salt per thousand barrels (PTB).

Figure 2:
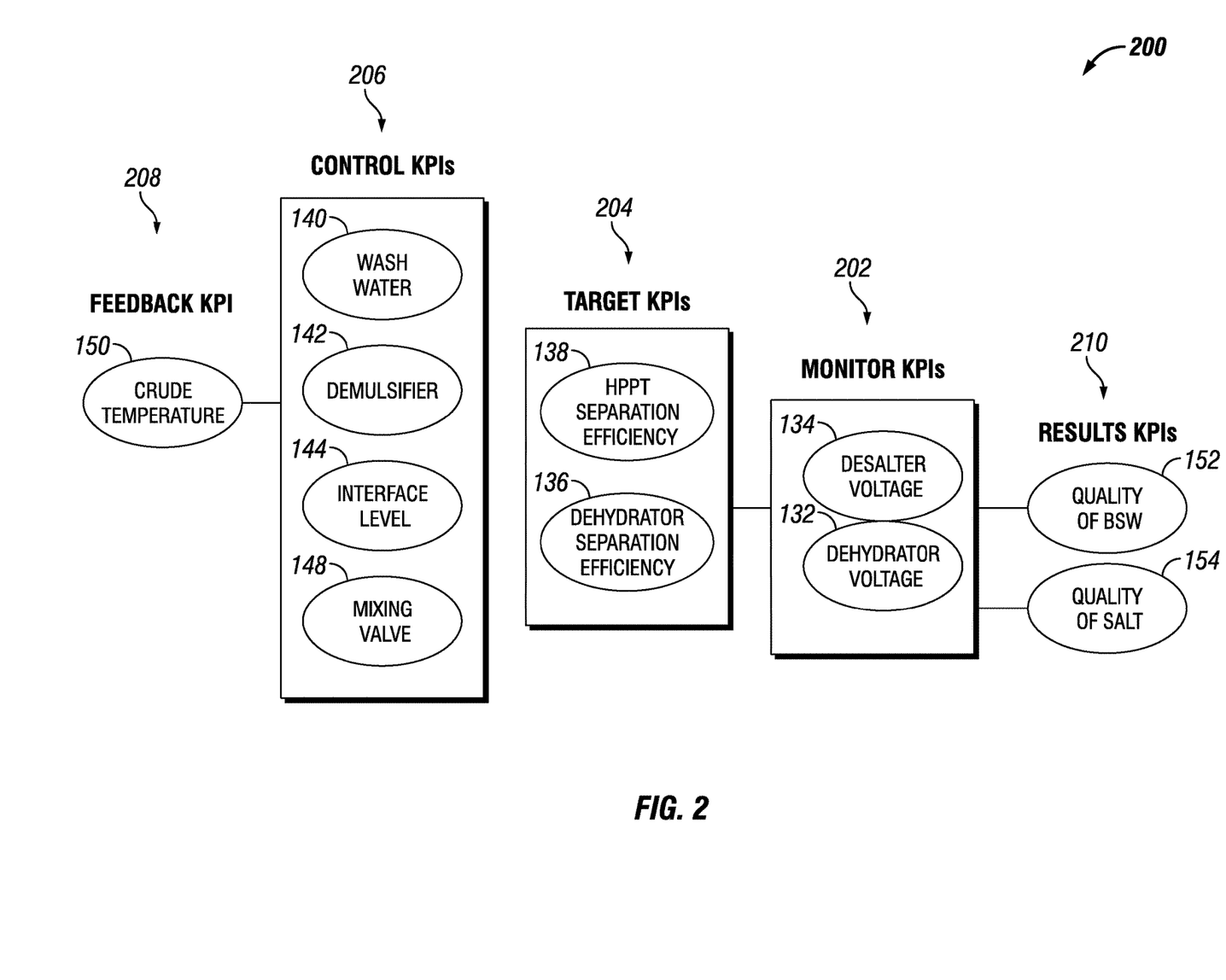
FIG. 2 is a block diagram illustrating the key performance indicators (KPIs) of FIG. 1 in accordance with an embodiment of the disclosure.

FIG. 2 is a diagram 200 of the various KPIs shown in FIG. 1 and a categorization of the KPIs based on the usage in the crude oil processing system 100. For example, FIG. 2 depicts the monitor KPIs 202, the target KPIs 204, the control KPIs 206, the feedback KPIs 208, and the results KPIs 210. As shown in FIG. 2, the monitor KPIs include the dehydrator voltage 132 and the desalter voltage 134, and the target KPIs 204 may include the dehydrator efficiency 136 and the HPPT efficiency 138. As also shown in FIG. 2, the control KPIs may include the wash water KPI 140, the demulsifier KPI 142, the dehydrator interface level KPI 144, the desalter interface level KPI 146), and the mixing valve KPI 148. Finally, as further shown in FIG. 2, the feedback KPI 208 includes the crude temperature KPI 150 and the results KPIs 210 include the BS&W KPI 152 and salt KPI 154.

The wash water KPI 140 and the demulsifier KPI 142 may be determined from various flowrates in the crude oil processing system 100. For example, the demulsifier KPI 142 may be calculated according to Equation 1:

$$\text{Demulsifier } KPI = \frac{\text{Demulsifier flowrate}}{\text{Dry crude flowrate} + \text{Produced water flowrate} - \text{wash water flowrate}} * 1000000 \quad (1)$$

Where the demulsifier flowrate is the mass flowrate of the demulsifier, the dry crude rate is the mass flowrate of the dry crude oil measured at a downstream shipping pump, and the wash water flowrate is the mass flowrate of the wash water. As will be appreciated, the various flowrates used in Equation 1 may be measured by instrument flowmeters positioned at appropriate locations.

The wash water KPI 140 may be calculated according to Equation 2:

$$\text{Wash water } KPI = \frac{\text{wash water flowrate}}{\text{dry crude flowrate}} * 100 \quad (2)$$

Where the wash water flowrate is the mass flowrate of the wash water and the dry crude flowrate is the mass flowrate of the dry crude oil measured at a downstream shipping pump. As will be appreciated, the various flowrates used in Equation 2 may be measured by instrument flowmeters positioned at appropriate locations.

The HPPTs efficiency KPI 138 and the dehydrator efficiency KPI 136 may also be determined from various flowrates in the crude oil processing system 100. For example, the HPPTs efficiency KPI 138 may be calculated according to Equation 3:

$$HPPTS \text{ efficiency } KPI = \frac{HPPTs \text{ water outlet flowrate}}{\text{produced water flowrate} - \text{wash water flowrate}} * 100 \quad (3)$$

Where the HPPTs water outlet flowrate is the mass flowrate of the separated water exiting the HPPTs, the wash water flowrate is the mass flowrate of the wash water, and the produced water flowrate is the mass flowrate of produced water. As used herein, "produced water" refers to water separated from the dehydrator and HPPTs that is routed to a water-oil separation unit then to produced water pumps for injection back in a reservoir or disposal wells. In some embodiments, the produced water flowrate is measured downstream from the produced water injection pumps by an instrument flowmeter. As will be appreciated, the HPPTs water outlet flowrate and wash water flowrate used in Equation 3 may be measured by instrument flowmeters positioned at appropriate locations The dehydrator efficiency KPI 136 may be calculated according to Equation 4:

$$\text{Dehydrator efficiency } KPI = \frac{\text{Dehydrator water outlet flowrate}}{\text{produced water flowrate} - \text{wash water flowrate}} * 100 \quad (4)$$

Where the dehydrator water outlet flowrate is the mass flowrate of the separated water exiting the dehydrator, the wash water flowrate is the mass flow rate of the wash water, and the produced water flowrate is the mass flowrate of produced water. As will be appreciated, the various flowrates used in Equation 4 may be measured by instrument flowmeters positioned at appropriate locations.

Figure 3:
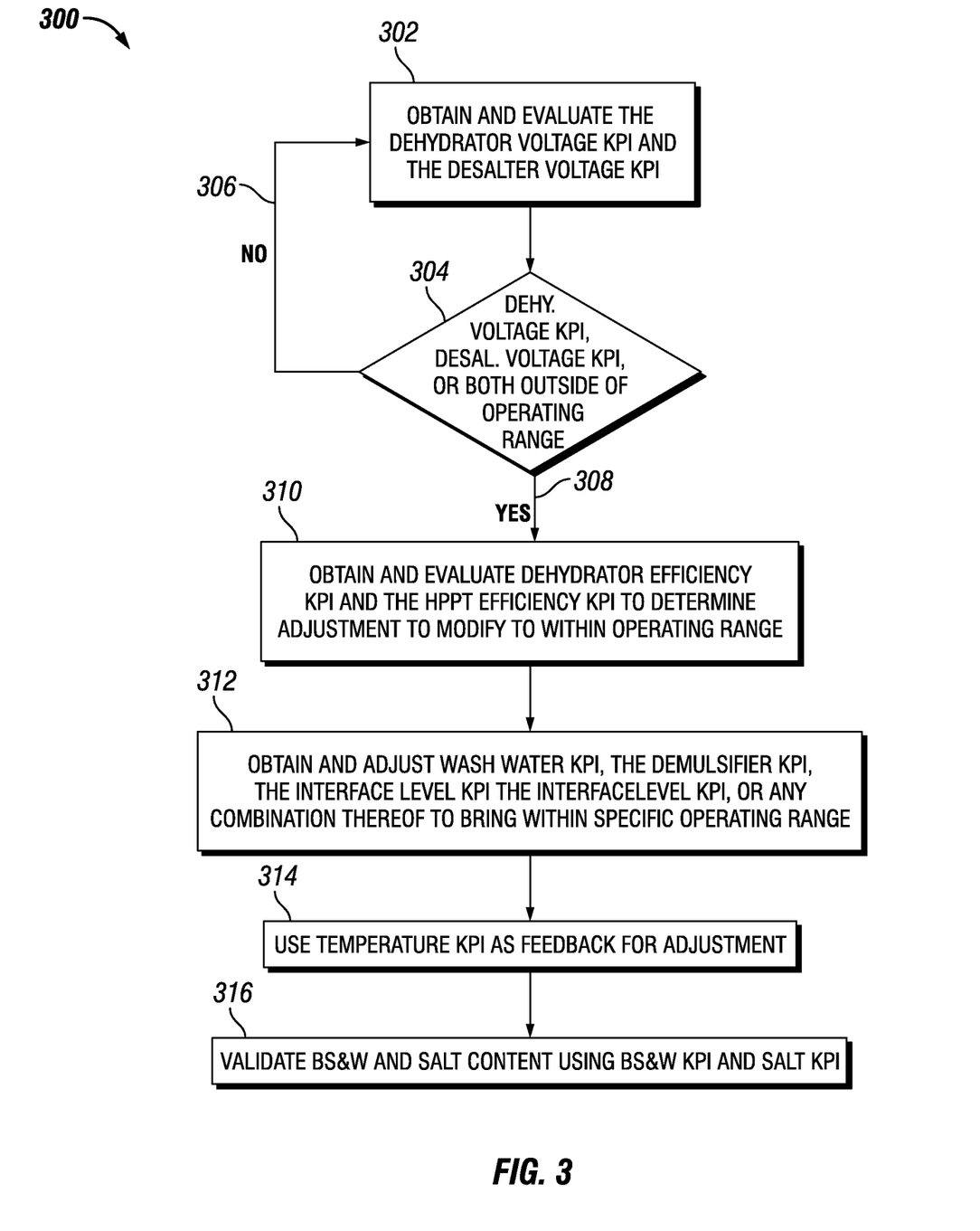
FIG. 3 if a flowchart of a process for monitoring and controlling the BS&W and salt content in accordance with an embodiment of the disclosure.

FIG. 3 depicts a process 300 for monitoring and controlling the BS&W and salt content of crude oil in accordance with an embodiment of the disclosure. In some embodiments, the process 300 may be performed periodically, that is at regular periods or at irregular periods. For example, in some embodiments the process 300 may be performed three times a day between equal time intervals, such that monitor KPIs are obtained between equal time intervals. In some embodiments, the process 300 may be performed once a day, twice a day, or more than three times a day. In some embodiments, the process 300 may be performed continuously, such that the dehydrator voltage KPI and desalter voltage KPI are continuously obtained and used to monitor the BS&W and salt content of crude oil. Additionally or alternatively, in some embodiments the process 300 may be performed on-demand, that is when requested such as by an operator of a crude oil processing system.

As shown in FIG. 3, a process 300 may include obtaining and evaluating the dehydrator voltage KPI and the desalter voltage KPI (block 302) to determine whether one or both of these KPIs are within a desired operating range (decision block 304). If both the dehydrator voltage KPI and the desalter voltage KPI are within the respective specific operating ranges, the process may return to obtaining and evaluating the dehydrator voltage KPI and the desalter voltage KPI (line 306). In other embodiments, the dehydrator voltage KPI and the desalter voltage KPI may each be compared to a respective threshold voltage value.

If one or both of these KPIs are not within a specific operating range (line 308), the dehydrator efficiency KPI and the HPPT efficiency KPI are obtained and evaluated to determine the adjustment to return the dehydrator efficiency KPI and the HPPT efficiency KPI to within their respective desired operating ranges (block 310). In some embodiments, only one of the dehydrator efficiency KPI or the HPPT efficiency KPI may be outside a respective operating range.

Based on the evaluation of the target KPIs, one or more of the wash water KPI, the demulsifier KPI, the dehydrator interface level KPI, the desalter interface level KPI, and the mixing valve KPI may be adjusted until the dehydrator efficiency KPI, the HPPT efficiency KPI, or both are within their respective desired operating ranges (block 312). In some embodiments, the temperature KPI may be used as a feedback parameter for adjustment of one or more of the wash water KPI, the demulsifier KPI, the dehydrator interface level KPI, the desalter interface level KPI, and the mixing valve KPI (block 314). As will be appreciated, each of the control KPIs referred to in block 312 may have a specific effect on operation of a crude oil processing system. For example, increasing the wash water KPI reduces the salt in the processed crude oil. In another example, the dehydrator interface level KPI and the desalter interface level KPI may, in some embodiments, be adjusted to meet interface levels specific to the design of a dehydrator and desalter respectively and to minimize impact on the respective dehydrator and desalter transformers. In yet another example, the demulsifier KPI may be increased to increase breakage of emulsions in the crude oil and increase separation in the HPPTs. In another example, the mixing valve KPI may be increased to increase the mixing energy to the crude oil and cause the formation of smaller water and salt droplets in the oil to increase contact with the wash water.

In some embodiments, the BS&W KPI and salt KPI may be used to validate the monitoring and control process 300. For example, the BS&W KPI and salt KPI may be periodically determined (for example, via direct instrument measurements or laboratory analysis) and compared against respective thresholds for BS&W content and salt content in the processed crude oil to ensure the processed crude oil meets a crude oil specification (block 316). In some embodiments, for example, a typical crude oil specification may specify a water content of no more than 0.2% by volume and a salt content of no more than 10 pounds of salt per thousand barrels (PTB).

Some embodiments of the monitoring and control process described herein may include three categories of operating ranges of each KPI. In some embodiments, the operating ranges may be visualized in a user interface by categorizing each operating range and associating each operating range with a visual indicator, such as a color, graphic, or other indicator. In some embodiments, the operating ranges and example colors may include the following:

Leading Proactive (LEP) (Green): This operating range corresponds to the most recommended range that will produce the best outcome from a KPI;

Lagging Proactive (LAP) (Yellow): This operating range corresponds to a latent loss of function. This range may correspond in an initial alarm that is signaled before reaching a partial or total loss of function, Lagging Reactive (LAR) (Red): This operating range corresponds to a total loss of function. This range indicates that a KPI is beyond its recommended limit and an immediate action is required.

Table 1 depicts the operating ranges for each of the KPIs that may be used in embodiments of the monitor and control process described herein:

TABLE 1

Example Operating Ranges for KPIs

| KPI | LEP | LAP | LAR |
|---|---|---|---|
| BS&W KPI (% volume) | 0.10 to 0.15 | 0.15 to 0.20 | 0.25 to 10 |
| Salt KPI (PTB) | 0 to 6 | 6 to 10 | 10 to 200 |
| Desalter Voltage KPI (volts) | 25 to 20 | 20 to 10 | 10 to 0 |
| Dehydrator Voltage KPI (volts) | 25 to 20 | 110 to 90 | 10 to 0 |
| Temperature KPI (° F.) | 120 to 110 | 25 to 20 | 90 to 80 |
| Demulsifier KPI (ppm) | 30 to 25 | 2.5-2 | 20 to 5 |
| Wash water KPI (%) | 3-2.5 | 50 to 40 | 2-0 |
| HPPTs Efficiency KPI (%) | 70 to 50 | 50 to 40 | 40 to 0 |
| Dehyd. Efficiency (%) | 30 to 50 | 50 to 60 | 60 to 100 |
| Dehyd. Interface Level KPI (%) | 60 to 70 | 75 to 80 | 80 to 85 |
| Desalter Interface level KPI (%) | 60 to 70 | 75 to 80 | 80 to 85 |
| Mixing valve KPI (psig) | 7-15 | 15-25 | 25-50 |

Figure 4:
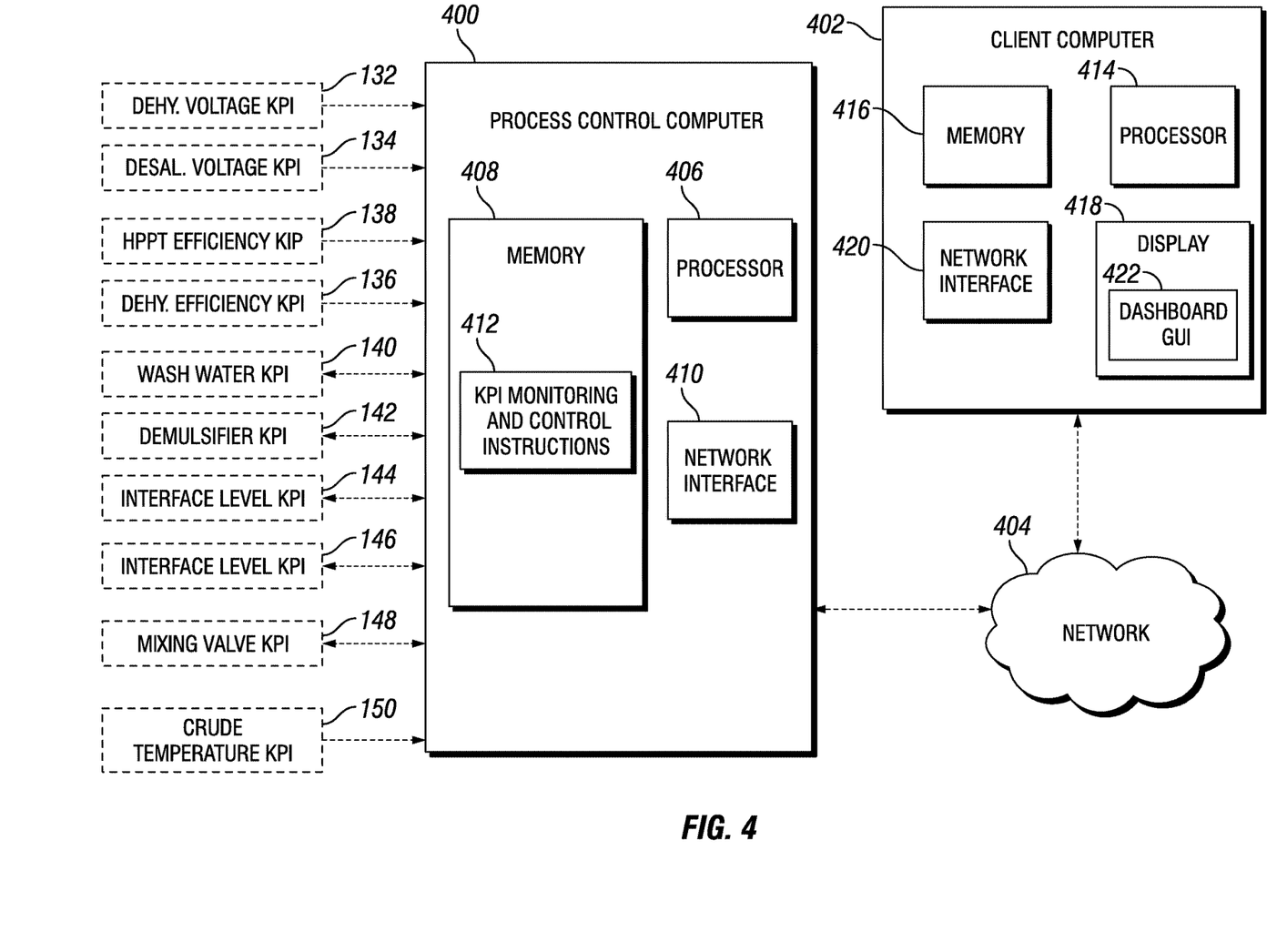
FIG. 4 depicts a block diagram of a process control computer in accordance with an embodiment of the disclosure.

In some embodiments, the monitoring and control process described in the disclosure may be implemented in a process control computer used in a crude oil processing system. FIG. 4 depicts a process control computer 400 that, for example, interacts with the KPIs of the crude oil processing system 100 described in FIG. 1 in accordance with an embodiment of the disclosure. In some embodiments, the process control computer 400 may interface with or be a part of a distributed control system (not shown) that controls various components that control and monitor a crude oil processing system. It should be appreciated that, in other embodiments, the monitoring and control process described in the disclosure may be implemented in a plant information system or other systems that are a part of or coupled to a crude oil processing system.

The process control computer 400 may be in communication with a client computer 402 via a network 404. In some embodiments, the process control computer 400 may be in communication with other components of a crude oil processing system, such as other process control computer computers and components that receive data from processes, a distributed control system, or both. It should be appreciated that various actions described herein may be implemented on multiple process control computer or distributed to different process control computer computers (for example, in some instances a first process control computer may obtain one or more KPIs of a crude oil processing system and a second process control computer may execute a monitoring and control process that evaluates KPIs and provides adjustment of control KPIs.

As shown in FIG. 4, the process control computer 400 may include a processor 406, a memory 408, and a network interface 410. It should be appreciated that the process control computer 400 may include other components that are omitted for clarity.

The processor 406 (as used the disclosure, the term "processor" encompasses microprocessors) and may include one or more processors having the capability to receive and process information, such as data received from sensors, a distributed control system, and other components and systems. In some embodiments, the processor 406 may include an application-specific integrated circuit (AISC). In some embodiments, the processor 406 may include a reduced instruction set (RISC) processor. Additionally, the processor 406 may include a single-core processors and multicore processors and may include graphics processors. Multiple processors may be employed to provide for parallel or sequential execution of one or more of the techniques described in the disclosure. The processor 406 may receive instructions and data from a memory (for example, memory 408).

The memory 408 (which may include one or more tangible non-transitory computer readable storage mediums) may include volatile memory, such as random access memory (RAM), and non-volatile memory, such as ROM, flash memory, a hard drive, any other suitable optical, magnetic, or solid-state storage medium, or a combination thereof. The memory 408 may be accessible by the processor 406. The memory 408 may store executable computer code. The executable computer code may include computer program instructions for implementing one or more techniques described in the disclosure, For example, the executable computer code may include the KPI monitoring and control instructions 412 executable by a processor (for example, the processor 406) to implement one or more embodiments of the present disclosure. In some embodiments, the KPI monitoring and control instructions 412 may implement one or more elements of process 300 described supra and illustrated in FIG. 3. For example, in some embodiments, the KPI monitoring and control instructions 412 may define a monitoring and control process that receives KPIs and determines an adjustment to one or more control KPIs to maintain a specific BS&W and salt content in processed crude oil. The received KPIs concentration may be stored in the memory 408 and, in some embodiments, provided to the client computer 402 as discussed below. In some embodiments, the memory 408 may also include instructions for the determination of various KPIs as described herein, such as the determination of the demulsifier KPI, the wash water KPI, the HPPTs efficiency KPI, and the dehydrator efficiency KPI.

The network interface 410 may provide for communication between the process control computer 400 and other devices, such as other process control computers and the client computer 402. The network interface 410 may include a wired network interface card (NIC), a wireless (for example, radio frequency) network interface card, or combination thereof. The network interface 410 may include circuitry for receiving and sending signals to and from communications networks, such as an antenna system, an RF transceiver, an amplifier, a tuner, an oscillator, a digital signal processor, and so forth. The network interface 410 may communicate with networks (for example, network 404), such as the Internet, an intranet, a wide area network (WAN), a local area network (LAN), a metropolitan area network (MAN) or other networks. Communication over networks may use suitable standards, protocols, and technologies, such as Ethernet Bluetooth, Wireless Fidelity (Wi-Fi) (for example, IEEE 802.11 standards), and other standards, protocols, and technologies. In some embodiments, the network interface 410 may enable communication over industrial control networks.

As shown in FIG. 4, the process control computer 400 may receive key process indicators such as dehydrator voltage KPI 132 and desalter voltage KPI 134 from the crude oil processing system 100. The process control computer 400 may also receive, for example, the HPPT efficiency KPI 138, the dehydrator efficiency KPI 136, the wash water KPI 140, the demulsifier KPI 142, the dehydrator interface level KPI 144, the desalter interface level KPI 146, the mixing valve KPI 148, and the crude temperature KPI 150. For example, the KPIs may be measured using or determined from suitable components arranged at various locations around the crude oil processing system 100. For example, as described above, the dehydrator efficiency 136, the HPPT efficiency 138, the wash water KPI 140, and the demulsifier KPI 142 may be determined using measurements from suitable components. Such components may include sensors such as flowmeters, temperature sensors (for example, thermometers or thermocouples), voltage sensors, pressure sensors, and so on. Such components may be a part of a distributed control system, or may be communication with a distributed control system via a suitable communication network.

A monitoring and control process defined by the monitoring and control process instructions 412 may obtain the KPIs and determine an adjustment of one or more control KPIs. As described above, in some embodiments the KPIs may be monitored periodically, continuously, or upon request, such as from an operator interfacing with the process control computer 400. In some embodiments, as described above, the monitoring and control process may provide a notification (for example, an alarm) if the dehydrator voltage KPI 134 or desalter voltage KPI 134 is within a specific operating range.

In some embodiments, the client computer 402 may be in communication with the process control computer 400 via the network 404. For example, the client computer 402 may provide process information to an operator and enable monitoring of the KPIs associated with the crude oil processing system 100. In such embodiments, the process control computer 400 may provide information to the client computer 406 about the crude oil processing system 100. For example, the process control computer 400 may provide the various values of KPIs obtained and determined by the process control computer 400 to the client computer 402. As shown in FIG. 4, the client computer 402 may include a processor 414, a memory 416, a display 418 and a network interface 420. It should be appreciated that the client computer 402 may include other components that are omitted for clarity.

The processor 414 (as used the disclosure, the term "processor" encompasses microprocessors) and may include one or more processors having the capability to receive and process information received from the process control computer 400. In some embodiments, the processor 414 may include an application-specific integrated circuit (AISC) or a reduced instruction set (RISC) processor. The processor 414 may also include a single-core processors and multicore processors and may include graphics processors. The processor 414 may receive instructions and data from the memory 416.

The memory 416 (which may include one or more tangible non-transitory computer readable storage mediums) may be accessible by the processor 414 and include volatile memory, such as random access memory (RAM), and non-volatile memory, such as ROM, flash memory, a hard drive, any other suitable optical, magnetic, or solid-state storage medium, or a combination thereof. The memory 416 may store executable computer code that may include, for example, computer program instructions for displaying a graphical user interface on the display 418 that provides information received from the process control computer 400.

The display 418 may include a cathode ray tube (CRT) display, liquid crystal display (LCD), an organic light emitting diode (OLED) display, or other suitable display. The display 418 may display a user interface (for example, a graphical user interface (GUI) that may display information received from the process control computer 400. In accordance with some embodiments, the display 418 may be a touch screen and may include or be provided with touch sensitive elements through which a user may interact with the user interface. In some embodiments, the display 418 may display a dashboard GUI 422 that displays various KPIs and respective user interface elements that indicate the respective operating ranges of the KPIs.

The network interface 420 may provide for communication between the client computer 402 and the process control computer 400 and, in some embodiments, between the client computer 402 and other devices. The network interface 420 of the client computer 402 may, in some embodiments, be similar to the network interface 410 of the process control computer 400. Accordingly, in some embodiments the network interface 420 includes a wired network interface card (NIC), a wireless (for example, radio frequency) network interface card, or combination thereof. The network interface 420 may include circuitry for receiving and sending signals to and from communications networks, such as an antenna system, an RF transceiver, an amplifier, a tuner, an oscillator, a digital signal processor, and so forth. The network interface 420 may communicate with networks (for example, network 404), such as the Internet, an intranet, a wide area network (WAN), a local area network (LAN), a metropolitan area network (MAN) or other networks. Communication over networks may use suitable standards, protocols, and technologies, such as Ethernet Bluetooth, Wireless Fidelity (Wi-Fi) (for example, IEEE 802.11 standards), and other standards, protocols, and technologies. In some embodiments, the network interface 420 may enable communication over industrial control networks.

FIG. 5 depicts a screen 500 of an example dashboard GUI in accordance with an embodiment of the disclosure. As shown in FIG. 5, the screen 500 of the example dashboard GUI may include a user interface element (for example, a table 502) that displays various text and includes graphics 504 (for example, a virtual gauge) that indicate the value of various KPIs and the current operating range. In the embodiments shown in FIG. 5, the operating ranges correspond to the three categories of operating ranges discussed above in paragraphs [0039]-[0041]. The table 502 may include a "Performance Measure" column 506 that provides the name of a KPI and a "Tag Source" column 508 that provides the identifier of an instrument tag of an instrument used to obtain the KPI. The table 502 of the example dashboard GUI also includes the numerical minimum and maximum values of the operating ranges. For example, the table 502 includes a "Range 1 Min" column 510 that corresponds to the minimum value of a first operating range, a "Range 1 Max" column 512 that corresponds to the minimum value of a first operating range, a "Range 2 Min" column 514 that corresponds to the minimum value of a second operating range, a "Range 2 Max" column 516 that corresponds to the maximum value of a second operating range, a "Range 3 Min" column 518 that corresponds to the minimum value of a third operating range, a "Range 3 Max" column 520 that corresponds to the maximum value of a third operating range. The table 502 includes a "Tag Value" column 522 that provides the value of the KPI for the KPI identified in the "Performance Measure" column 506 for the row. Finally, the table includes a "Radial Gauge Display" column 524 that provides the graphics 504 for the KPI identified in the "Performance Measure" column 506 for the row The graphics 504 may, in some embodiments, include visual indicators (for example, colors) that indicate the operating range of a KPI provided in the table 502. In some embodiments, each operating range category may be associated with a color. For example, as discussed above, a Leading Proactive (LEP) operating range may be indicated by the color green, a lagging Proactive (LAP) may be indicated by the color yellow, and a Lagging Reactive operating range may be indicated by the color red. The graphical indicator 504 may indicate each of the operating ranges by its respective color and may also include a virtual needle that indicates the present value of the KPI identified in the "Performance Measure" column 506 for the row. By way of example, row 526 corresponds to a dehydration separation efficiency KPI as indicated by the text "Dehydration Separation Efficiency" in the "Performance Measure" column 506. The values "Range 1 Min" and "Range 1 Max" values provided in columns 510 and 512 of row 522 are 0.00 and 45.00 respectively. This operating range is indicated by the green portion of graphical indicator 526. The values "Range 2 Min" and "Range 2 Max" values provided in columns 514 and 516 of row 522 are 40.0000 and 55.0000 respectively. This operating range is indicated by the yellow portion of graphical indicator 528. Finally, the values "Range 3 Min" and "Range 3 Max" values provided in columns 518 and 520 of row 522 are 55.0000 and 100.0000 respectively. As shown in graphical indicator 523, the virtual needle shows that the value of 54.07 indicated in the Tag Value" column 522 is within the "Range 2 Min" and "Range 2 Max" indicated by the yellow portion of graphical indicator 524.

Ranges may be expressed in the disclosure as from about one particular value, to about another particular value, or both. When such a range is expressed, it is to be understood that another embodiment is from the one particular value, to the other particular value, or both, along with all combinations within said range.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used described in the disclosure are for organizational purposes only and are not meant to be used to limit the scope of the description.

What is claimed is:

1. A method of processing crude oil, comprising:
   obtaining a first voltage associated with a desalter of a crude oil processing system;
   obtaining a second voltage associated with a dehydrator of a crude oil processing system, wherein an output stream from the dehydrator is provided to the desalter;
   evaluating at least one of the first voltage and the second voltage as an indicator of the salt concentration in crude oil; and
   adjusting at least one of a plurality of control parameters in response to the evaluation to modify at least one of a separation efficiency of a high pressure production trap (HPPT) of the crude oil processing system and a separation efficiency of the dehydrator,
   the plurality of control parameters comprising a wash water parameter, a demulsifier parameter, an interface level of the dehydrator, an interface level of the desalter, and a mixing valve parameter, wherein the mixing valve parameter comprises a differential pressure across a mixing valve positioned to mix wash water, a demulsifier, and the dehydrator output stream.

2. The method of claim 1, wherein evaluating at least one of the first voltage and the second voltage comprises comparing at least one of the first voltage and the second voltage to a voltage threshold.

3. The method of claim 1, wherein evaluating at least one of the first voltage and the second voltage comprises comparing at least one of the first voltage and the second voltage to a first operating voltage range, a second operating voltage range, and a third operating voltage range.

4. The method of claim 1, wherein the wash water parameter comprises a ratio of a wash water flowrate to a dry crude oil flowrate, wherein the dry crude oil flowrate comprises a flowrate of crude oil downstream from the desalter.

5. The method of claim 1, wherein the dehydrator output stream is mixed with a demulsifier before being provided to the desalter, wherein the demulsifier parameter comprises a ratio of a demulsifier flowrate to a sum of a dry crude oil flowrate and a produced water flowrate minus a wash water flowrate, wherein the dry crude oil flowrate comprises a flowrate of crude oil downstream from the desalter and the produced water flowrate comprises a sum of the flowrate of separated water from the dehydrator and separated water from the HPPT, after the separated water from the dehydrator and the separated water from the HPPT is provided to a water-oil separation unit.

6. The method of claim 1, wherein the separation efficiency of the high pressure production trap (HPPT) comprises the ratio of HPPT water outlet flowrate to a difference between a produced water flowrate and a wash water flowrate, wherein the produced water flowrate comprises a sum of the flowrate of separated water from the dehydrator and separated water from the HPPT, after the separated water from the dehydrator and the separated water from the HPPT is provided to a water-oil separation unit.

7. The method of claim 1, wherein the separation efficiency of the dehydrator comprises the ratio of dehydrator water outlet flowrate to a difference between a produced water flowrate and a wash water flowrate, wherein the produced water flowrate comprises a sum of the flowrate of separated water from the dehydrator and separated water from the HPPT, after the separated water from the dehydrator and the separated water from the HPPT is provided to a water-oil separation unit.

8. The method of claim 1, wherein adjusting at least one of the plurality of control parameters comprises adjusting at least one of the plurality of control parameters in response to the temperature of a crude oil feed to the crude oil processing facility.

9. The method of claim 1, wherein adjusting the at least one of a plurality of control parameters comprises adjusting at least one of the plurality of control parameters until the adjusted control parameter is within an operating range associated with the adjusted control parameter.

10. A non-transitory computer-readable storage medium having executable code stored thereon for controlling the processing crude oil, the executable code comprising a set of instructions that causes a processor to perform operations comprising:
    obtaining a first voltage associated with a desalter of a crude oil processing system;
    obtaining a second voltage associated with a dehydrator of a crude oil processing system, wherein an output stream from the dehydrator is provided to the desalter;
    evaluating at least one of the first voltage and the second voltage as an indicator of the salt concentration in crude oil; and
    adjusting at least one of a plurality of control parameters in response to the evaluation to modify at least one of a separation efficiency of the high pressure production trap (HPPT) of the crude oil processing system and a separation efficiency of the dehydrator,
    the plurality of control parameters comprising a wash water parameter, a demulsifier parameter, an interface level of the dehydrator, an interface level of the desalter, and a mixing valve parameter, wherein the mixing valve parameter comprises a differential pressure across a mixing valve positioned to mix wash water, a demulsifier, and the dehydrator output stream.

11. The non-transitory computer-readable storage medium of claim 10, wherein evaluating at least one of the first voltage and the second voltage comprises comparing at least one of the first voltage and the second voltage to a voltage threshold.

12. The non-transitory computer-readable storage medium of claim 10, wherein evaluating at least one of the first voltage and the second voltage comprises comparing at least one of the first voltage and the second voltage to a first operating voltage range, a second operating voltage range, and a third operating voltage range.

13. The non-transitory computer-readable storage medium of claim 10, wherein the wash water parameter comprises a ratio of a wash water flowrate to a dry crude oil flowrate, wherein the dry crude oil flowrate comprises a flowrate of crude oil downstream from the desalter.

14. The non-transitory computer-readable storage medium of claim 10, wherein the dehydrator output stream is mixed with a demulsifier before being provided to the desalter.

15. The non-transitory computer-readable storage medium of claim 10, wherein the separation efficiency of the high pressure production trap (HPPT) comprises the ratio of HPPT water outlet flowrate to a difference between a produced water flowrate and a wash water flowrate, wherein the produced water flowrate comprises a sum of the flowrate of separated water from the dehydrator and separated water from the HPPT, after the separated water from the dehydrator and the separated water from the HPPT is provided to a water-oil separation unit.

16. The non-transitory computer-readable storage medium of claim 10, wherein the separation efficiency of the dehydrator comprises the ratio of dehydrator water outlet flowrate to a difference between a produced water flowrate and a wash water flowrate, wherein the produced water flowrate comprises a sum of the flowrate of separated water from the dehydrator and separated water from the HPPT, after the separated water from the dehydrator and the separated water from the HPPT is provided to a water-oil separation unit.

17. The non-transitory computer-readable storage medium of claim 10, wherein adjusting at least one of the plurality of control parameters comprises adjusting at least one of the plurality of control parameters in response to the temperature of a crude oil feed to the crude oil processing facility.

18. The non-transitory computer-readable storage medium of claim 10, wherein adjusting the at least one of a plurality of control parameters comprises adjusting at least one of the plurality of control parameters until the adjusted control parameter is within an operating range associated with the adjusted control parameter.

19. The non-transitory computer-readable storage medium of claim 10, the operations comprising providing a graphical user interface on a display coupled to the processor, the graphical user interface comprising a user interface element graphically indicating the value of the parameter relative to a plurality of operational ranges.

20. The non-transitory computer-readable storage medium of claim 19, wherein the user interface element comprises a first color associated with a first range of the plurality of operating ranges, a second color associated with a second range of the plurality of operating ranges, and a third color associated with a third range of the plurality of operating ranges.

21. A crude oil processing system, comprising:
a desalter;
a dehydrator;
a high pressure production trap (HPPT);
a processor;
a non-transitory computer-readable memory coupled to the processor and having executable code stored thereon for controlling the processing of crude oil, the executable code comprising a set of instructions that causes the processor to perform operations comprising:
obtaining a first voltage associated with the desalter;
obtaining a second voltage associated with the dehydrator;
evaluating at least one of the first voltage and the second voltage as an indicator of the salt concentration in the crude oil; and
adjusting at least one of a plurality of control parameters in response to the evaluation to modify at least one of a separation efficiency of the HPPT and a separation efficiency of the dehydrator,
the plurality of control parameters comprising a wash water parameter, a demulsifier parameter, an interface level of the dehydrator, an interface level of the desalter, and a mixing valve parameter, wherein the mixing valve parameter comprises a differential pressure across a mixing valve positioned to mix wash water, a demulsifier, and the dehydrator output stream.

22. The system of claim 21, wherein evaluating at least one of the first voltage and the second voltage comprises comparing at least one of the first voltage and the second voltage to a first operating voltage range, a second operating voltage range, and a third operating voltage range.

23. The system of claim 21, wherein the wash water parameter comprises a ratio of a wash water flowrate to a dry crude oil flowrate, wherein the dry crude oil flowrate comprises a flowrate of crude oil downstream from the desalter.

24. The system of claim 21, wherein the dehydrator output stream is mixed with a demulsifier before being provided to the desalter, wherein the dry crude oil flowrate comprises a flowrate of crude oil downstream from the desalter and the produced water flowrate comprises, wherein the produced water flowrate comprises a sum of the flowrate of separated water from the dehydrator and separated water from the HPPT, after the separated water from the dehydrator and the separated water from the HPPT is provided to a water-oil separation unit.

25. The system of claim 21, wherein the separation efficiency of the high pressure production trap (HPPT) comprises the ratio of HPPT water outlet flowrate to a difference between a produced water flowrate and a wash water flowrate, wherein the produced water flowrate comprises, wherein the produced water flowrate comprises a sum of the flowrate of separated water from the dehydrator and separated water from the HPPT, after the separated water from the dehydrator and the separated water from the HPPT is provided to a water-oil separation unit.

26. The system of claim 21, wherein the separation efficiency of the dehydrator comprises the ratio of dehydrator water outlet flowrate to a difference between a produced water flowrate and a wash water flowrate, wherein the produced water flowrate comprises, wherein the produced water flowrate comprises a sum of the flowrate of separated water from the dehydrator and separated water from the HPPT, after the separated water from the dehydrator and the separated water from the HPPT is provided to a water-oil separation unit.

* * * * *